(12) United States Patent
Negishi et al.

(10) Patent No.: US 11,738,997 B2
(45) Date of Patent: Aug. 29, 2023

(54) METHOD AND APPARATUS FOR PRODUCING HALOGEN OXYACID SOLUTION

(71) Applicant: TOKUYAMA CORPORATION, Yamaguchi (JP)

(72) Inventors: Takayuki Negishi, Yamaguchi (JP); Takafumi Shimoda, Yamaguchi (JP); Akihiro Saito, Yamaguchi (JP); Naoki Matsuda, Yamaguchi (JP); Kenichi Kakizono, Yamaguchi (JP); Takeshi Kawano, Yamaguchi (JP); Masayuki Moriwaki, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 265 days.

(21) Appl. No.: 17/357,232

(22) Filed: Jun. 24, 2021

(65) Prior Publication Data

US 2021/0403323 A1 Dec. 30, 2021

(30) Foreign Application Priority Data

Jun. 25, 2020 (JP) .................................. 2020-109267

(51) Int. Cl.
  *C01B 11/06* (2006.01)
  *B01F 25/43* (2022.01)

(52) U.S. Cl.
  CPC .............. *C01B 11/06* (2013.01); *B01F 25/43* (2022.01)

(58) Field of Classification Search
  CPC .................................. C01B 11/06; B01F 25/43
  See application file for complete search history.

(56) References Cited

U.S. PATENT DOCUMENTS

2002/0060202 A1 5/2002 Fukunaga et al.
2005/0176603 A1 8/2005 Hsu

FOREIGN PATENT DOCUMENTS

| | | |
|---|---|---|
| EP | 3 798 207 | 3/2021 |
| JP | 2002-161381 | 6/2002 |
| JP | 2003-119494 | 4/2003 |
| JP | 2005-227749 | 8/2005 |
| JP | 2009-81247 | 4/2009 |
| WO | 2019/225541 | 11/2019 |

*Primary Examiner* — Sikarl A Witherspoon
(74) *Attorney, Agent, or Firm* — WENDEROTH, LIND & PONACK, L.L.P.

(57) ABSTRACT

The present invention provides industrially advantageous production method and production apparatus, with respect to production of a halogen oxyacid solution. There is solved by a method for producing a halogen oxyacid solution, comprising continuously supplying an organic alkaline solution and halogen to a static mixer and mixing them, to thereby continuously obtain a halogen oxyacid generated.

16 Claims, 1 Drawing Sheet

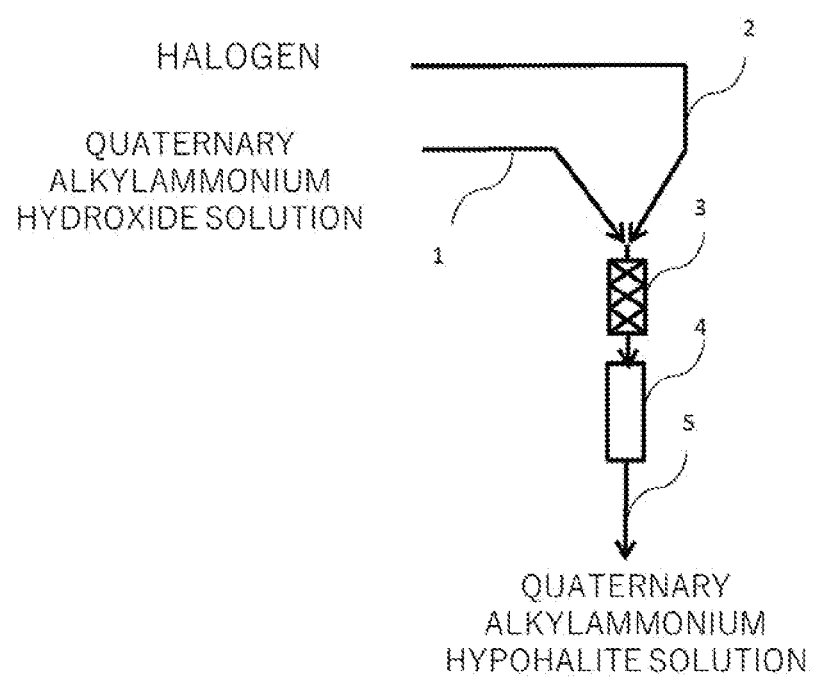

METHOD AND APPARATUS FOR PRODUCING HALOGEN OXYACID SOLUTION

TECHNICAL FIELD

The present invention relates to a method for producing a halogen oxyacid solution, for example, a quaternary alkylammonium hypochlorite solution. More specifically, the present invention provides a method and apparatus for industrially advantageously producing a halogen oxyacid solution excellent in storage stability, such as a quaternary alkylammonium hypochlorite solution.

BACKGROUND ART

In recent years, the miniaturization of design rules for semiconductor elements has been in progress, and requirements for impurity control in semiconductor element production processes have been severer. Since impurities generated in semiconductor element production processes are different with respect to each of the production processes, it is important to identify any contamination source with respect to each of the production processes and to control the concentration of impurities serving as such any contamination source.

Large-diameter semiconductor wafers whose diameters are more than 300 mm are used in order to enhance the production efficiency of semiconductor elements. Such large-diameter semiconductor wafers are large in areas of end surface parts and back surface parts where no electronic devices are manufactured, as compared with small-diameter semiconductor wafers. Thus, metal wiring materials and barrier metal materials (hereinafter, also sometimes collectively referred to as "metal material and the like") are easily attached onto not only semiconductor wafer surface parts on which semiconductor elements are to be formed, but also end surface parts and back surface parts, in the step of forming metal wirings and the step of forming barrier metals. This results in an increase in amount of excess metal material and the like attached onto end surface parts and back surface parts of large-diameter semiconductor wafers, as compared with small-diameter wafers.

Such excess metal material and the like attached onto end surface parts and back surface parts of semiconductor wafers contaminate the interior of production apparatuses, in the form of metal or metal oxide particles, in the step of ashing by oxygen and the step of dry etching by plasma, which are the steps after formation of metal wirings and barrier metals, and cause cross-contamination. Thus, such metal material and the like attached onto end surface parts and back surface parts are needed to be removed before introduction into the next step.

Noble metals typified by platinum and ruthenium, among such metal material and the like, are hardly oxidized, dissolved, and removed in subsequent etching step and washing step. Thus, such noble metals are preferably removed from semiconductor wafers, in preference to other metal materials. In particular, ruthenium is heavily used in wiring materials for use in semiconductor elements with a design rule of 10 nm or less because ruthenium is capable of reducing the resistance value as compared to a case where copper is used in such wiring materials, and therefore is demanded to be rapidly removed from any unrequired section.

In general, there is proposed a washing method using hypochlorite high in oxidation power, as a washing liquid of a semiconductor wafer. Specifically, a method using an aqueous sodium hypochlorite solution is proposed (see Patent Documents 1 and 2).

However, such a method using an aqueous sodium hypochlorite solution as a washing liquid causes many sodium ions to be naturally contained m the washing liquid. As a result, sodium ions may be easily attached to, for example, semiconductor wafers, leading to deterioration in semiconductor production efficiency.

On the contrary, there has been developed a washing liquid without sodium as an essential component, which uses a hypochlorous acid solution (see Patent Document 3) or an aqueous quaternary alkylammonium hypochlorite solution (see Patent Document 4).

However, such a washing liquid using hypochlorous acid (see Patent Document 3) is used for washing a substrate provided with a metal film and a metal oxide film, and is not used particularly for removal of any noble metal. Thus, such a washing liquid is not suitable for washing off any film of metal such as noble metal/metal oxide.

The washing liquid containing an aqueous tetramethylammonium hypochlorite solution, described in Patent Document 4, is also a washing liquid for use in washing off of photoresist and residues, and is not intended for washing off any coating of metals such as copper and aluminum, containing ruthenium. It is specifically revealed in Examples that a metal film is hardly etched. Patent Document 5 discloses etching performance with excellent storage stability, due to optimization of the pH of a quaternary alkylammonium hypochlorite solution.

However, production methods described in Patent Documents 4 and 5 each involve a batch reaction which produces a tetramethylammonium hypochlorite solution by supplying a chlorine gas to a tetramethylammonium hydroxide solution for a certain period. Patent Document 4 describes the production method in which the supplying period of the chlorine gas is about 6 minutes and a 250 ml Erlenmeyer flask is used as a reactor in order to produce 160 g of a tetramethylammonium hypochlorite solution, and the method has the problem of a low production efficiency per volume, as an industrial production method.

RELATED ART DOCUMENT

Patent Document

Patent Document 1: Japanese Patent Application Publication No. 2002-161381
Patent Document 2: Japanese Patent Application Publication No. 2009-081247
Patent Document 3: Japanese Patent Application Publication No. 2003-119494
Patent Document 4: Japanese Patent Application Publication No. 2005-227749
Patent Document 5: International Publication WO 2019/225541

SUMMARY OF THE INVENTION

Problems to be Solved by the Invention

Accordingly, an object of the present invention is to provide a method for producing a halogen oxyacid solution by a reaction of an organic alkaline solution and halogen, the method involving industrially advantageously producing the solution at an increased production efficiency per reaction volume, and a production apparatus therefor.

Means for Solving the Problems

The inventors have made further studies in order to achieve the object, and as a result, there is provided a method for efficiently producing an organic alkaline solution, as compared with a batch reaction, by performing an operation for continuously supplying an organic alkaline solution and halogen to a static mixer and mixing them, at least one or more times, and continuously retrieving a halogen oxyacid solution generated.

In other words, the present invention is configured as follows.

Aspect 1. A method for producing a halogen oxyacid solution, comprising continuously supplying an organic alkaline solution and halogen to a static mixer and mixing them, to thereby continuously obtain a halogen oxyacid generated.

Aspect 2. The method for producing a halogen oxyacid solution according to Aspect 1, wherein a ratio of raw materials supplied is controlled so that a pH at 25° C. of a mixed liquid of the organic alkaline solution and halogen passed through the static mixer is more than 10.5 and less than 14.1.

Aspect 3. The method for producing a halogen oxyacid solution according to Aspect 2, wherein the pH at 25° C. of the mixed liquid is 12.0 or more and 13.8 or less.

Aspect 4. The method for producing a halogen oxyacid solution according to any one of Aspects 1 to 3, wherein the halogen is supplied at multiple stages.

Aspect 5. The method for producing a halogen oxyacid solution according to any one of Aspects 1 to 4, wherein the mixing is performed at multiple stages.

Aspect 6. The method for producing a halogen oxyacid solution according to any one of Aspects 1 to 5, wherein the static mixer is an ejector, a collision type static mixer, or a Sulzer static mixer.

Aspect 7. The method for producing a halogen oxyacid solution according to any one of Aspects 1 to 6, wherein the halogen oxyacid solution is retrieved without being circulated in a production process.

Aspect 8. The method for producing a halogen oxyacid solution according to any one of Aspects 1 to 7, wherein a pH at 25° C. of the organic alkaline solution is 10.5 or more and 14.5 or less.

Aspect 9. The method for producing a halogen oxyacid solution according to any one of Aspects 1 to 8, wherein the organic alkali is onium hydroxide and the halogen oxyacid is halogen oxyacid onium.

Aspect 10. The method for producing a halogen oxyacid solution according to Aspect 9, wherein the onium hydroxide is quaternary alkylammonium hydroxide and the halogen oxyacid onium is quaternary alkylammonium hypohalite.

Aspect 11. The method for producing a halogen oxyacid solution according to any one of Aspects 1 to 10, wherein the quaternary alkylammonium hydroxide is tetramethylammonium hydroxide.

Aspect 12. The method for producing a halogen oxyacid solution according to any one of Aspects 1 to 11, wherein the halogen is chlorine, bromine, hypochlorous acid, hypobromous acid, chlorous acid, chlorous acid, chloric acid, bromic acid, iodine, hypoiodous acid, iodous acid, or iodic acid.

Aspect 13. The method for producing a halogen oxyacid solution according to any one of Aspects 1 to 12, wherein the halogen is chlorine.

Aspect 14. A halogen oxyacid solution production apparatus comprising a static mixer, an organic alkaline solution supply means and a halogen supply means to the static mixer, and a reaction liquid retrieve means for outwardly retrieviting a reaction liquid from the static mixer, wherein an organic alkaline solution and halogen are continuously supplied respectively from the organic alkaline solution supply means and the halogen supply means to the static mixer, and mixed, to thereby generate a halogen oxyacid solution as a reaction liquid, and the reaction liquid is continuously rertrieved by the reaction liquid retrieve means.

Aspect 15. The halogen oxyacid solution production apparatus according to Aspect 14, further comprising one or more separate static mixers downstream of the static mixer and upstream of the reaction liquid retrieve means, and further comprising a halogen supply means for supplying halogen to each of the separate static mixers.

Aspect 16. The halogen oxyacid solution production apparatus according to Aspect 14 or 15, further comprising a heat exchanger that performs heat exchange of the reaction liquid.

Effect of the Invention

According to the present invention, there can be provided a method and an apparatus, in which a halogen oxyacid solution is industrially advantageously produced by efficiently increasing the production efficiency per reaction volume and thus enhancing the amount of production, as compared with a batch reaction.

BRIEF DESCRIPTION OF THE DRAWING

FIG. 1 is a schematic view showing one mode of a production apparatus according to an embodiment of the present invention.

MODE FOR CARRYING OUT THE INVENTION

<Method for Producing Halogen Oxyacid>
(Reaction Mode)

Next, a main feature of the present embodiment is to adopt a mode where halogen is continuously supplied to a static mixer and a halogen oxyacid solution generated is continuously retrieved in a flow channel where flowing through of an organic alkaline solution is conducted. Hereinafter, the halogen oxyacid solution generated is sometimes referred to as "reaction liquid" or "mixed liquid". Such mixing of the organic alkaline solution with halogen enables the amount of production per volume to be increased in the state where any side reaction is reduced by placement of the static mixer in the flow channel. An aspect is also preferable where a heat exchanger is placed in the flow channel, for removal of reaction heat and heat of absorption generated in a reaction of the organic alkaline solution with halogen, to thereby perform removal of heat of the reaction liquid.

A conventional batch type reaction mode, which corresponds to a process involving adding halogen into an organic alkaline solution loaded in a reactor, thus not only has likely caused an increase in pH of a reaction liquid at the initial stage of the reaction, but also has resulted in a long liquid stay time in the reactor, and thus has easily caused decomposition of halogen oxyacid at a high pH. Any halogen oxyacid generated in a high pH region, in which a decomposed product generated by decomposition of such halogen oxyacid is generated, thus is problematic in terms of stability. In this regard, if the organic alkaline solution and halogen are reacted in the flow channel and the reaction liquid is continuously retrieved, the liquid stay time can be decreased and such halogen oxyacid is inhibited from being decomposed. Additionally, the amount of production per volume can be increased.

The pH of the reaction liquid of organic alkali and halogen to be supplied in the flow channel is suitably more than 10.5 and less than 14.1. The pH of the reaction liquid of the organic alkaline solution and halogen is more preferably 12.0 or more and 13.8 or less.

The reaction liquid in the flow channel is thus preferably homogenized rapidly. The method for homogenizing the reaction liquid in the present invention involves mixing the organic alkaline solution and halogen by the static mixer. The ratio of raw materials supplied is preferably controlled so that the pH of the mixed liquid (halogen oxyacid solution) passed through the static mixer is preferably more than 10.5 and less than 14.1, more preferably 12.0 or more and 13.8 or less. The pH in the present invention is a value at 25° C. unless particularly noted. The pH is also a value with respect to a mixed liquid immediately after passing through the static mixer, in other words, located at an exit of the static mixer.

Any static mixer can be used without particular limitations as long as the mixer allows the pH of the mixed liquid after passing through the static mixer to be preferably more than 10.5 and less than 14.1, more preferably 12.0 or more and 13.8 or less. In a case where chlorine gas, chlorine ion, or an oxoacid of chlorine is used as halogen, it is important for an increase in yield of chlorine to rapidly mix the organic alkaline solution and halogen by use of the static mixer.

The pH of the mixed liquid passed through the static mixer is the pH of the reaction liquid retrieved from the static mixer where final passing through is conducted, in the production method of the present invention. In a case where the reaction liquid is mixed by a plurality of different such static mixers or the reaction liquid is circulated and then mixed again in the static mixer where passing through of the reaction liquid is conducted once, the pH is defined as the pH of the reaction liquid underwent final mixing by the static mixer.

The yield of chlorine mentioned above is determined from the ratio (%) of the number of moles of hypochlorite ion generated, to the number of moles of a chlorine molecule supplied. In a case where the total of chlorine added is reacted (no occurrence of decomposition), the yield of chlorine is 100%. In a case where the hypochlorite ion is decomposed during the reaction, the yield of chlorine is reduced.

The static mixer here used can be a known commercially available product without any limitations. Specific examples can include a Y-tube, an ejector, a plate collision static mixer, a cup collision static mixer, and Kenic-, Etoflo HV-, Sulzer SMXL-, Sulzwr SMX-. Sulzer SMV-, Tray Hi- mixer-, Bran and Lubbe N-form-, Komax-, Lightnin In- liner-, Ross ISG-, and Prematechnik PMR-static mixers which are shown as mixer forms in Handbook of Chemistry and Engineering, revised sixth edition.

There is a suitable aspect where such static mixers are disposed at multiple stages in order to enhance mixing performance of such static mixers. Such static mixers can be disposed at multiple stages to thereby perform a reaction at multiple stages.

In a case where such static mixers are disposed at, for example, two stages, an aspect can be exemplified where not only a reaction liquid passed through a first static mixer is supplied to a second static mixer, but also halogen is also supplied to a second static mixer. The halogen to be supplied to the second static mixer can be the same as or different from the halogen to be supplied to the first static mixer, in terms of the composition thereof. The number of such static mixers is not limited only to two, and two or more, for example, three, four, or five such static mixers can be disposed. The upper limit is not particularly limited, and examples thereof can include 10 or less. In a case where the $n^{th}$ static mixer is disposed, an aspect can be exemplified where a pipe is provided downstream of the $n-1^{th}$ static mixer, the pipe is connected to the $n^{th}$ static mixer, and the $n^{th}$ halogen supply means is provided so as to be connected to the $n^{th}$ static mixer (n is, for example, 2, 3, 4, 5, 6, 7, 8, 9 or 10).

In a case where the halogen to be supplied is different from the halogen to be supplied to the first static mixer, in terms of the composition thereof, the conditions thereof preferably fall within the conditions applied to the halogen to be supplied to the first static mixer. The conditions of the amount of the halogen to be supplied and the flow rate (speed) of the halogen to be supplied also preferably fall within the conditions applied to the halogen to be supplied to the first static mixer.

In the production method of the present invention, the halogen oxyacid solution as the reaction liquid can be allowed to flow through so as to be circulated in the production process. The circulation of the reaction liquid in the production process is such that the reaction liquid flowing out from the initial static mixer is again supplied not to the retrieve pipe of the reaction liquid, but the static mixer where passing through of the liquid is conducted once. The reaction liquid can be supplied to the static mixer where passing through of the liquid is conducted once, and fresh halogen can be supplied, to thereby react unreacted organic alkali and halogen remaining in the reaction liquid.

In the production method of the present invention, the halogen oxyacid solution as the reaction liquid can also be retrieved without being circulated in the production process. Such retrieve is to retrieve the reaction liquid obtained by passing through one or more such static mixers, without again supplying of the liquid to the static mixer where passing through of the liquid is conducted once. The "production process" means a process including from the initial supplying of the organic alkaline solution and halogen until retrieve of the resulting reaction liquid, and can include any step described below.

In a case where the halogen is gaseous, a static mixer favorable in gas-liquid dispersion performance is preferable because such a gas is dispersed as fine bubbles in the solution and dissolution thereof can be promoted in a pipe located downstream. Examples of such a static mixer include an ejector, a plate static mixer, a cup collision static mixer, Kenics static mixer and Sulzer static mixer.

A further preferable static mixer here selected is one where any fluid after mixing is easily in a flow state of bubbles, and an ejector, a plate static mixer, a cup collision static mixer, Sulzer static mixer is particularly preferable.

(Organic Alkaline Solution)

The organic alkaline solution to be supplied to the static mixer can be any of an aqueous solution where an organic alkali is dissolved in water or a solution where an organic alkali is dissolved in a non-aqueous solvent. The organic alkaline solution can be obtained by, for example, dissolving an organic alkali in water or a non-aqueous solvent, or diluting a commercially available organic alkaline solution to a desired concentration. Examples of the non-aqueous solvent can include a known organic solvent that can dissolve an organic alkali. Specific examples include alcohol and glycol, and in particular, methanol and propylene glycol are preferable. Among such solvents, the solvent is preferably water from the viewpoint that an industrially available and high-purity organic alkaline solution is available. The concentration of the organic alkaline solution is not particularly limited, but a high organic alkali concentration leads to precipitation of a salt, to result in a solid. Accordingly, the concentration of the organic alkaline solution is preferably 0.01 mass % or more and 30 mass % or less, more preferably 0.05 mass % or more and 27.5 mass % or less, still more preferably 0.1 mass % or more and 25 mass % or less.

An organic alkaline solution to be used usually contains atmospherically derived carbon dioxide. Such carbon dioxide is present as carbonate ion or bicarbonate ion in the solution. The carbon dioxide concentration is not particularly limited, and is preferably 0.001 ppm or more and 500 ppm or less (on a mass basis), more preferably 0.005 ppm or more and 300 ppm or less, still more preferably 0.01 ppm or more and 100 ppm or less, when converted to carbonate ion. The carbon dioxide concentration in the organic alkaline solution can be 0.001 ppm or more and 500 ppm or less, to thereby allow for suppression of fluctuations in the pH of the resulting halogen oxyacid solution. As a result, the halogen oxyacid solution can be enhanced in storage stability. The organic alkaline solution having such a carbon dioxide concentration, here used, can be a commercially available product.

In a case where, for example, a quaternary alkylammonium hydroxide solution is prepared as the organic alkaline solution to be used, hypochlorite ion generated in a reaction step is decomposed if ammonia or/and an amine compound is/are present in the solution. In general, a commercially available quaternary alkylammonium hydroxide solution contains amine. Such a quaternary alkylammonium hydroxide solution is used to thereby cause the hypochlorite ion generated in a reaction step to be reacted with such amine, to result in a decrease in hypochlorite ion concentration. In a case where the amine compound is tertiary amine, secondary amine, primary amine and ammonia generated in a reaction with the hypochlorite ion, are also reacted with the hypochlorite ion, to thereby result in a significant decrease in hypochlorite ion concentration. In particular, tertiary amine not only is rapidly progressively reacted with the hypochlorite ion, but also results in a significant decrease in hypochlorite ion concentration even if present in a trace amount thereof.

It is known that, for example, a commercially available tetramethylammonium hydroxide solution contains several tens to several hundred mass ppm of trimethylamine. Since trimethylamine is reacted with hypochlorite ion to generate dimethylamine and monomethylamine, such a tetramethylammonium hydroxide solution is not suitable for use because of causing a decrease in hypochlorite ion concentration.

Accordingly, the concentration of such ammonia or/and amine compound contained in the quaternary alkylammonium hydroxide solution is preferably low, and is specifically preferably 20 mass ppm or less. A concentration of 20 mass ppm or less can allow suppressing a decrease in hypochlorite ion concentration in a reaction step, to thereby result in an enhancement in stability of the resulting quaternary alkylammonium hypochlorite solution. The amine concentration in the present invention is the total value of the respective concentrations of tertiary amine, secondary amine, primary amine, and ammonia contained in the solution. A quaternary alkylammonium hydroxide solution decreased in amine, here used, can be suitably, for example, a tetramethylammonium hydroxide solution for use in semiconductor applications, a tetramethyammoniuml hydroxide solution from which ammonia or/and an amine compound is/are removed by, for example, distillation or ion exchange, or a tetramethylammonium hydroxide solution subjected to a decompression treatment or a degassing treatment with an inert gas. In particular, a tetramethylammonium hydroxide solution for use in semiconductor applications is more preferable from the viewpoint that an industrial product is available and the amine concentration is kept low. Furthermore, a tetramethylammonium hydroxide solution for use in semiconductor applications, which is subjected to distillation, ion exchange, a decompression treatment, and a degassing treatment, is most preferable because the amine concentration is low.

The solvent for preparing the organic alkaline solution can be an aqueous solution with only water as a solvent or a non-aqueous solution mixed with an organic solvent. The solvent can be appropriately changed depending on the application of a solution containing halogen oxyacid, and the subject to be washed off. In a case where the subject to be washed off is ruthenium, such washing off can be sufficiently made by only water as the solvent, and thus an aqueous organic alkaline solution can be prepared.

The organic alkaline solution in the present embodiment is preferably an aqueous solution of onium hydroxide, and examples of such onium hydroxide include ammonium hydroxide, phosphonium hydroxide, sulfonium hydroxide, iminium hydroxide including a multiple bond, and diazonium hydroxide. In particular, an aqueous solution of ammonium hydroxide, which is often present in the form of a relatively stable compound, is more preferable. The quaternary alkylammonium hydroxide solution is preferably a solution of quaternary alkylammonium hydroxide having an alkyl group having carbon number from 1 to 10, more preferably a solution of quaternary alkylammonium hydroxide having an alkyl group having carbon number from 1 to 5. Specific examples of such quaternary alkylammonium hydroxide are tetramethylammonium hydroxide, tetraethylammonium hydroxide, tetrabutylammonium hydroxide, and choline and so on. Such quaternary alkylammonium hydroxide can be used singly or in combination of two or more kinds thereof. The respective carbon numbers of four alkyl groups included in such quaternary alkylammonium hydroxide can be the same as or different from one another.

Various conditions in the above and following description, for example, the range of the organic alkali concentration in the organic alkaline solution supplied to the static mixer and the range of the pH thereof, and the range of the organic alkali concentration in the reaction liquid and the range of the pH thereof, can be applied to a case using any specific example of the organic alkali.

(Process for Producing Reaction Liquid Containing Halogen Oxyacid by Mixing Organic Alkaline Solution and Halogen in Static Mixer)

In a process for producing a reaction liquid containing halogen oxyacid by mixing an organic alkaline solution and halogen and reacting them, the reaction liquid containing halogen oxyacid, generated by mixing in the static mixer, tends to be decreased in pH after passing through the static mixer. In the present embodiment, the lower limit of the pH of the organic alkaline solution serving as a raw material is more than 10.5, preferably 11.0 or more, still more preferably 11.5 or more, particularly preferably more than 12.0, in consideration of conditions of a filtration step described below and the solubility of organic alkali. The upper limit of the pH of the organic alkaline solution is determined depending on the organic alkali concentration, and is preferably 14.5 or less.

The organic alkaline solution for use in the present embodiment can include any metal, specifically, sodium, potassium, aluminum, magnesium, iron, nickel, copper, silver, cadmium, and lead. Herein, the content of such each metal is preferably 0.01 ppb or more and 20 ppb or less. While the content of such each metal contained in the organic alkaline solution used can be, of course, less than 0.01 ppb, such an organic alkaline solution is difficult to obtain.

Thus, an organic alkaline solution satisfying the content of such each metal within the range can be obtained easily, and removal/decrease of such metal impurities can be easily facilitated during production of the reaction liquid containing halogen oxyacid and in a filtration step after the production. Although the reason why such metal impurities can be removed/decreased by the filtration step is not clear, it is considered that such metal impurities are present in some degrees to thereby generate not a colloidal article which is hardly removed by filtration, but impurity particles having a certain size, and thus can be removed by filtration. Thus, the organic alkaline solution for use in the present embodiment can be decreased in pH to result in removal/decrease of a solid material of such metal impurities by a filtration step, and thus can be suitably used even if not an ultrahigh-purity organic alkaline solution. For increasing this effect and more efficiently removing/decreasing impurities which are in the form of ions in alkaline condition, the content of each of metals such as sodium, potassium, aluminum, magnesium, iron, nickel, copper, silver, cadmium, and lead contained in the organic alkaline solution is more preferably 0.01 ppb or more and 5 ppb or less, still more preferably 0.01 ppb or more and 2 ppb or less.

The above organic alkaline solution can be a commercially available product. In particular, a photoresist developer of a semiconductor element, which is increased in purity by an electrolytic method and/or by contact with an ion exchange resin or the like, can be suitably used as an organic alkaline solution. Such a commercially available product, which is diluted with a solvent containing no metal impurities, like ultrapure water, can also be used.

The rate of supply of the organic alkaline solution supplied to the static mixer can be, for example, 0.01 m/s or more and 10 m/s or less, more preferably 0.2 nm/s or more and 3 m/s or less, depending on the concentration of the organic alkaline solution.

(Reaction Occurring by Contacting Organic Alkaline Solution with Halogen)

For example, in a case where quaternary alkylammonium hydroxide is used as an organic alkali, the solution thereof is contacted and reacted with halogen, to thereby replace hydroxide ion of the quaternary alkylammonium hydroxide with hypohalite ion generated by halogen, and generate a quaternary alkylammonium hypohalite solution.

The halogen for use in the present embodiment is not particularly limited as long as it serves as a halogen source like a single halogen element or oxoacid of a halogen element, and a commercially available product can be adopted. Specific examples of the halogen can include chlorine, bromine, hypochlorous acid, hypobromous acid, chlorous acid, bromous acid, chloric acid, bromic acid, iodine, hypoiodous acid, iodous acid, or iodic acid. In a case where chlorine or bromine is used, for example, any gas thereof, chlorine water, or bromine water can be used. In particular, a chlorine gas is preferably used.

In particular, one having high purity can be used, for example, one for use in etching of a semiconductor material, or one for use in a raw material of a semiconductor material. One having high purity, in particular, one having a low water content is preferable, and specifically one having a water content of 10 volume ppm or less (on a mass basis) is preferably used. The reason for this, although is not clear, is considered as follows. For example, in a case where a chlorine gas is used to produce a quaternary alkylammonium hypochlorite solution, the chlorine gas is usually exported via a pipe. Thus, it is considered that, if a large amount of water is present, hydrogen chloride is generated to corrode the pipe and a metal member of a flowmeter or the like and corroded metal impurities tend to be introduced together with the chlorine gas, into the system. Thus, one where the water content contained in the chlorine gas is 10 volume ppm or less is preferably used. As will be understood, a commercially available chlorine gas can be used as it is, or can be contacted with a drying material or the like immediately before introduction into the reaction system and thus decreased in water content contained in the chlorine gas. The lower limit of the water content contained in the chlorine gas is not particularly limited, and is 0.1 volume ppm in consideration of industrial availability.

In a case where the chlorine gas is used, an aspect is preferable where an apparatus called purifier is disposed in the middle of the pipe to remove any gaseous contaminant (metal and/or the like).

In a case where a chlorine gas is used as the halogen in the present embodiment, the concentration of carbon dioxide contained in the chlorine gas is not particularly limited, and is preferably 0.001 volume ppm or more and 80 volume ppm or less, more preferably 0.005 volume ppm or more and 50 volume ppm or less, still more preferably 0.01 volume ppm or more and 2 volume ppm or less. In a case where the carbon dioxide concentration in the chlorine gas is within the range of 0.001 volume ppm or more and 80 volume ppm or less, fluctuations in the pH of the resulting quaternary alkylammonium hypochlorite solution can be suppressed. As a result, the quaternary alkylammonium hypochlorite solution can be enhanced in storage stability. The chlorine gas having such a carbon dioxide concentration can be a commercially available product.

The amount of the halogen used in the present embodiment (the number of moles of the halogen used) is not particularly limited, and can be appropriately determined in consideration of, for example, the concentration and the total amount of the organic alkali used, and the concentration and the total amount of the resulting halogen oxyacid. For example, in a case where hypochlorous acid, hypobromous acid, chlorous acid, bromous acid, chloric acid, or bromic acid is used as the halogen and a quaternary alkylammonium hydroxide solution is used as the organic alkaline solution, the amount of the halogen, per liter of the quaternary alkylammonium hydroxide solution, is preferably from 8 μmol to 3.4 mol. The halogen can be used within the range, to thereby stably produce halogen oxyacid. Although an amount of usage of more than 3.4 mol per liter of the quaternary alkylammonium hydroxide solution can be set, the pH of the resulting halogen oxyacid tends to be reduced to result in a tendency to easily cause halogen oxyacid to be decomposed. On the other hand, an amount of less than 8 μmol leads to a low halogen oxyacid concentration, to result in deterioration in production efficiency. The amount per liter of the quaternary alkylammonium hydroxide solution is thus preferably from 8 μmol to 3.4 mol, more preferably from 80 μmol to 3.2 mol, still more preferably from 800 μmol to 3.0 mol in consideration of industrial production. The amount of the halogen can also be here determined in consideration of the pH of the resulting solution, namely, the pH of the resulting quaternary alkylammonium hypochlorite solution.

Next, an exemplary embodiment of the present invention will be described, which relates to a method where the quaternary alkylammonium hydroxide solution is used as the organic alkaline solution and the chlorine gas is used as the halogen, to thereby allow them to be contacted with each other, in the present embodiment. In the following description, while it is sometimes supposed without any notification that the quaternary alkylammonium hydroxide solution is used as the organic alkaline solution and the chlorine gas is used as the halogen, such a case is described only as one example.

The supplying method adopted as the method for supplying the chlorine gas to the flow channel can be a known method. The method can be appropriately determined so that flow of the organic alkaline solution is not inhibited, because mixing is performed by a static mixer disposed after supplying of the chlorine gas.

A reaction in a production apparatus according to an embodiment of the present invention is preferably performed in a closed system in order to avoid carbon dioxide from being incorporated into a reaction system. The amount of the halogen gas (the total amount of the chlorine gas) is not particularly limited in the present embodiment, and the amount of the chlorine gas per liter of the quaternary alkylammonium hydroxide solution, on 0° C./1 atm conversion, is preferably 0.1 mL or more and 37000 mL or less, and can be 10 mL or more and 1000 mL or less. The chlorine gas is used within the range, to thereby allow for suppression of rapid fluctuations in the pH in the reaction system and allow removal/decrease of metal impurities in a filtration step to be facilitated. While the amount of the chlorine gas per liter of the quaternary alkylammonium hydroxide solution, on 0° C./1 atm conversion, can be more than 37000 mL, the quaternary alkylammonium hydroxide solution tends to be larger in reduction/variation in pH and furthermore an unreacted chlorine gas tends to remain. In a case where the amount is less than 0.1 mL, sufficient hypochlorite ion tends not to be able to be produced. Thus, the amount of the chlorine gas per liter of the quaternary alkylammonium hydroxide solution, on 0° C./1 atm conversion, is preferably within the range of 0.1 mL or more and 37000 mL or less, in consideration of industrial production. It is noted that the amount of the chlorine gas can also be determined in consideration of the pH of the resulting solution, namely, the pH of the resulting quaternary alkylammonium hypochlorite solution.

The chlorine gas is preferably supplied into the static mixer at the following speed. The flow rate (speed) of the chlorine gas supplied is preferably 0.45 mmol/min or more and 1380 mmol/min or less per liter of the quaternary alkylammonium hydroxide solution from the viewpoint that rapid reduction in pH is not caused and a chlorine gas having no involvement in any reaction is decreased. The range can be satisfied to impart sufficient reactivity and allow the quaternary alkylammonium hypochlorite solution to be produced without any rapid reduction/variation in pH. The amount of the chlorine gas supplied to the reaction system is more preferably 0.45 mmol/min or more and 1200 mmol/min or less, still more preferably 0.90 mmol/min or more and 1000 mmol/min or less.

The organic alkali in the present embodiment can further cantain a bromine salt. In such an organic alkali containing a bromine salt, halogen and the organic alkali are reacted to generate, for example, hypohalous acid and halide. The hypohalous acid is reacted with bromide ion, hypobromite ion, bromite ion, bromate ion, or perbromate ion contained in the bromine salt, or a bromine molecule generated from the bromine salt, to thereby impart fresh halogen oxyacid. The reaction of the hypohalous acid and the ion, or of the hypohalous acid and the bromine molecule can be any reaction where halogen is added to a solution containing the bromine salt and the organic alkali to thereby generate fresh halogen oxyacid, and can be, for example a redox reaction, a disproportionation reaction, or a radical reaction.

The bromine salt in the present invention is a salt containing a bromine atom, and is, for example, hypobromite, bromite, bromate, perbromate, or bromide. Examples of the bromide can include hydrogen bromide, lithium bromide, sodium bromide, potassium bromide, rubidium bromide, cesium bromide, ammonium bromide, and onium bromide. The onium bromide here mentioned is a compound formed from onium ion and bromide ion. The onium ion here refers to, for example, a positive ion such as imidazolium ion, pyrrolidinium ion, pyridinium ion, piperidinium ion, ammonium ion, phosphonium ion, fluoronium ion, chloronium ion, bromonium ion, iodonium ion, oxonium ion, sulfonium ion, selenonium ion, telluronium ion, arsonium ion, stibonium ion, or bismuthonium ion. A compound that generates hypobromite or hypobromite ion in a treatment liquid can also be suitably used as a bromine-containing compound. Examples of such a compound can include a bromohydantoin compound, a bromoisocyanuric acid compound, a bromosulfamic acid compound, and a bromochloramine compound, but are not limited thereto. More specific examples of the compound include 1-bromo-3-chloro-5,5-dimethylhydantoin, 1,3-dibromo-5,5-dimethylhydantoin, and tribromoisocyanuric acid.

For the purpose of more specific illustration, in a case where the bromine salt is tetramethylammonium bromide, the organic alkali is tetramethylammonium hydroxide and the halogen is chlorine, a reaction of the bromine salt, the organic alkali and the halogen is exemplified as follows. The chlorine gas is blown into an aqueous solution containing tetramethylammonium bromide and tetramethylammonium hydroxide to thereby react tetramethylammonium hydroxide and chlorine, to thereby generate hypochlorous acid and chloride. The hypochlorous acid is partially reacted with bromide ion contained in tetramethylammonium bromide in the solution and the bromide ion is directly oxidized, to thereby yield hypobromous acid. As a result, an aqueous solution containing hypochlorous acid, hypobromous acid, chloride (tetramethylammonium chloride), unreacted tetramethylammonium bromide, and tetramethylammonium hydroxide is obtained. In other words, halogen oxyacid containing two halogen oxyacids (hypochlorous acid and hypobromous acid) is obtained. In a case where the number of moles of a chlorine molecule is smaller than the number of moles of tetramethylammonium bromide in the solution containing the bromine salt and the organic alkali, an aqueous solution containing hypobromous acid, chloride (tetramethylammonium chloride), unreacted tetramethylammonium bromide, and tetramethylammonium hydroxide is obtained.

The concentration of the bromine salt optionally added to the organic alkali is not particularly limited, and can be, for example, within the range from 0.1 μmol/L to 10 mol/L. A solution containing a plurality of halogen acids, thus obtained, can be suitably used for semiconductor production.

(Reaction Temperature)

The range of the reaction temperature in the production method of the present embodiment is preferably −35° C. or more and 45° C. or less, more preferably −15° C. or more and 40° C. or less, still more preferably −5° C. or more and 35° C. or less. In a case where the reaction temperature is within the range, the quaternary alkylammonium hydroxide solution and chlorine can be sufficiently reacted, to obtain a quaternary alkylammonium hypochlorite solution at a high production efficiency. In a case where the reaction temperature is less than −35° C., the quaternary alkylammonium hydroxide solution is started to be solidified, and is not sufficiently reacted with chlorine. In a case where the reaction temperature is more than 45° C., hypochlorite ion generated in the quaternary alkylammonium hydroxide solution is decomposed by heat. In particular, in a case where the pH in the reaction is 13.8 or more, an increase in reaction temperature remarkably causes decomposition of the hypochlorite ion. The production efficiency of quaternary alkylammonium hypochlorite can be evaluated in terms of the ratio of the number of moles of the generated hypochlorite ion to the number of moles of a chlorine molecule supplied as a raw material. As described above, the production method of the present embodiment can produce a quaternary alkylammonium hypochlorite solution which is excellent in storage stability, for example, which can sufficiently maintain washing and removal abilities even after a lapse of 10 days from production. As clear therefrom, the quaternary alkylammonium hypochlorite solution obtained in the production method of the present embodiment is excellent in storage stability and can be suitably used in a production process of a semiconductor element.

(Materials of Inside Surfaces of Static mixer and Pipe)

In the present embodiment, the quaternary alkylammonium hydroxide solution and the chlorine gas are contacted in the static mixer, to thereby produce the quaternary alkylammonium hypochlorite solution. First, a predetermined amount of the quaternary alkylammonium hydroxide solution can be introduced into such a reactor in advance, and then the chlorine gas can be introduced to as to be in contact with the quaternary alkylammonium hydroxide solution.

In the present embodiment, a surface in the static mixer and that in the pipe of the production apparatus, with which the quaternary alkylammonium hydroxide solution is to be contacted, can be formed by an organic polymer material, and thus incorporation of the impurities containing metal (metal impurities) can be more decreased.

The reaction is preferably performed under a light shielding environment, and specifically, the static mixer is preferably a static mixer in which light is shielded. The chlorine gas present in the static mixer may be excited by light to generate chlorine radical Such chlorine radical, when generated, may have any influence on the quaternary alkylammonium hydroxide and the quaternary alkylammonium hypochlorite generated in the reaction, present in the static mixer, to result in decomposition. The quaternary alkylammonium hypochlorite by itself may be decomposed by light, and thus it is preferable to subject the pipe and the like with which the static mixer is provided, to light shielding.

In the present embodiment, in a case where the solvent here used is an organic solvent, the static mixer and the pipe preferably each have an explosion-proof structure. Thus, the solvent of the quaternary alkylammonium hydroxide solution is preferably water in order to allow for a simple apparatus configuration.

In the present embodiment, the organic polymer material for use in the inside surfaces of the static mixer and the pipe can be, for example, a vinyl chloride resin (flexible or hard vinyl chloride resin), a nylon resin, a silicone resin, a polyolefin resin (polyethylene, polypropylene), or a fluororesin. In particular, a fluororesin is preferable in consideration of, for example, ease of molding, solvent resistance, and less elution of impurities.

The fluororesin is not particularly limited as long as the resin is a resin (polymer) containing a fluorine atom, and a known fluororesin can be used. Examples include polytetrafluoroethylene, polychlorotrifluoroethylene, polyvinylidene fluoride, a tetrafluoroethylene-hexafluoropropylene copolymer, a tetrafluoroethylene-perfluoroalkyl vinyl ether copolymer, a tetrafluoroethylene-ethylene copolymer, a chlorotrifluoroethylene-ethylene copolymer, and a cyclized polymer of perfluoro(butenyl vinyl ether). In particular, a tetrafluoroethylene-perfluoroalkyl vinyl ether copolymer is preferably used in consideration of, for example, availability of the reactor by itself and productivity.

Examples of the method for forming the inside surfaces of the static mixer and the pipe by the organic polymer material in the present embodiment include a method for forming the entire static mixer and the entire pipe by the organic polymer material, and a method for covering only inside surfaces of a static mixer and a pipe each made of glass or stainless steel, with the organic polymer material.

Use after washing can also be made in order that a metal component is prevented from being eluted from the organic polymer material. Specifically, sufficient washing with an acid such as high purity nitric acid or hydrochloric acid (for example, washing by immersion in a solution having an acid concentration of 1 mol/L for 12 hours) and further washing with ultrapure water or the like are preferable. The inside surfaces of the static mixer and the pipe, formed by the organic polymer material, are preferably washed according to the above method before the quaternary alkylammonium hydroxide solution and the chlorine gas are reacted, in order that the reaction is stably performed.

In the present embodiment, as long as surfaces of the static mixer and the pipe, to be contacted with the quaternary alkylammonium hydroxide solution, are formed by the organic polymer material, other portions thereof can be made of glass, stainless steel, or stainless steel passivated. Herein, such surfaces and portions are preferably formed by the same organic polymer material, although not essential because there are few influences.

In the present embodiment, the quaternary alkylammonium hydroxide solution and the chlorine gas can be contacted in the static mixer, and the chlorine gas is preferably introduced into the quaternary alkylammonium hydroxide solution. The range of the reaction temperature here is not particularly limited, and is preferably the same as that of the above reaction temperature. The presence of carbon dioxide in the reaction system tends to cause the pH of the resulting quaternary alkylammonium hypochlorite solution to be reduced. Thus, no carbon dioxide is preferably contained in the reaction system in consideration of stable production. Specifically, the quaternary alkylammonium hydroxide solution, the chlorine gas, and the like, which are decreased in amount of carbon dioxide, are preferably used. The reaction is preferably performed in the presence of an inert gas decreased in amount of carbon dioxide (for example, in the presence of a nitrogen gas). The reaction can be performed in such conditions to thereby allow for suppression of a reduction in the pH of the resulting quaternary alkylammonium hypochlorite solution, to result in an enhancement in storage stability.

The amine concentration in a liquid phase portion in the reaction step is preferably kept at 100 mass ppm or less. As described in the section (Organic Alkaline Solution), amine is contained in the quaternary alkylammonium hydroxide solution to result in a reduction in concentration of the hypochlorite ion generated in the reaction step.

The hypochlorite ion generated in the reaction is reacted with quaternary alkylammonium ion at a high pH to generate tertiary amine, and thus, as the reaction progresses, the amine concentration in the liquid phase portion is increased. In other words, the amine concentration in the liquid phase portion in the reaction step tends to be higher than the amine concentration before the reaction step. However, the amine concentration in the liquid phase portion in the reaction step can be kept at 100 mass ppm or less to thereby suppress a reduction in concentration of the hypochlorite ion, to result in an enhancement in storage stability.

<Filtration Step>

In a production method according to an embodiment of the present invention, as the quaternary alkylammonium hydroxide solution and the chlorine gas are contacted to generate the quaternary alkylammonium hypochlorite solution, the pH of the solution in the reaction system is reduced. A solid material containing metal impurities may be here precipitated, and a method of a preferable embodiment preferably further includes a step of filtration for removal/decrease of the solid material. In other words, the quaternary alkylammonium hypochlorite solution obtained in the middle of the reaction or by supplying of the chlorine gas until the predetermined concentration is obtained is preferably filtered. The filtration step can be performed after a storage step described below or after dilution. The metal component collected by filtration in the filtration step may differ depending on the pH of the quaternary alkylammonium hypochlorite solution.

Specifically, in a case where the pH of the quaternary alkylammonium hypochlorite solution is 13.5 or less, preferably in a case where the pH of the solution is more than 12.5 and 13.5 or less, hydroxides of magnesium, iron, cadmium, and the like, and oxides of nickel and silver are solidified and thus such impurities can also be removed/decreased by performing the filtration step. In a case where the pH of the quaternary alkylammonium hypochlorite solution is 12.5 or less, preferably in a case where the pH of the solution is 9.0 or more and 12.5 or less, not only the impurities, but also oxides of copper and lead are solidified and thus such impurities can also be removed/decreased by performing the filtration step. The pH of the solution may vary depending on the temperature. The pH is here a value at 25° C., as a guide. The liquid temperature in the filtration step actually performed is not limited to 25° C., and the step is preferably performed at 20° C. or more and 28° C. or less, still more preferably 23° C. or more and 25° C. or less. Such a solid material of metal impurities is generated even if a purity of the quaternary alkylammonium hydroxide solution to be used and the chlorine gas is high. In particular, even in a case where the inside surface of the static mixer is formed by the organic polymer material, the solid material is sometimes generated. Although the reason for this is not clear, it is presumed that the chlorine gas which is a high-corrosive gas is used and thus metal impurities from any location in the reaction apparatus contaiminate the reaction system.

The filtration step can be performed at any pH at which a metal compound to be removed/decreased is solidified. Thus, the step can be performed only once, or can also be performed multiple times at each pH. Herein, a plurality of filtration filters different in pore size are prepared with respect to each pH and filtration is performed in the order of a filtration filter larger in pore size, to result in an enhancement in filtration efficiency. Specifically, such filtration can be performed by removing coarse particles at the first stage and removing fine particles at the second stage. Herein, particles whose sizes are 1 µm or more and 100 µm or less, of the solid material containing the metal component, for example, simple metal impurities, metal oxide, metal hydroxide, and/or a colloidal article, may be hereinafter simply referred to as "coarse particles". On the other hand, particles whose sizes are 0.01 µm or more and less than 1 µm may be hereinafter simply referred to as "fine particles". The particle size of the solid material refers to an equivalent circle diameter in laser diffraction.

The filtration step is not particularly limited, and can be performed by use of a known filtration apparatus or filtration filter. Herein, a surface in the filtration apparatus, with which the quaternary alkylammonium hypochlorite solution can be contacted, is preferably formed by the organic polymer material in order not to increase an unnecessary metal component. Such an organic polymer here used can be the same as exemplified above.

Specifically, the filtration filter is preferably a filtration filter made of an organic polymer material or an inorganic material. Examples can include respective filtration filters made of polyolefin (polypropylene, polyethylene, ultra-high molecular weight polyethylene), polysulfone, cellulose acetate, polyimide, polystyrene, the fluororesin, and/or quartz fiber. The filtration filter used is preferably a combination of a membrane positively charged and a membrane negatively charged. The reason for this is because many metal oxides and metal hydroxides are negatively charged in an alkaline atmosphere and such metal components can be more effectively removed by a filtration filter positively charged by electrostatic adsorption. Some of such metal components are present in the form of cation and are positively charged. Thus, a filtration filter negatively charged can remove a metal component effectively ionized by electrostatic adsorption. A filter having ion exchange ability or chelate formation ability, for example, a filter including an ion exchange resin or a chelate exchange resin can also be used. A plurality of such filters can be combined and used.

The pore size of the filtration filter is not particularly limited, and a filtration filter where the pore size is 1 µm or more, or a microfiltration filter can be used for removal of coarse particles. A microfiltration filter where the pore size is 0.01 µm or more and less than 1 µm, an ultrafiltration filter, or a nanofiltration membrane can be used for removal of fine particles.

The above filtration filters can be commercially available products. Specifically, "Fluorogard ATX filter (pore size 0.05 µm)", "QuickChange ATE filter (pore size 0.03 µm)", "Torrento ATE filter (pore size 0.02 µm)", "QuickChange ATE filter (pore size 0.03 µm)", and "Fluoroline P-1500 (pore size 0.05 µm, 0.1 µm)", which are made of polytetrafluoroethylene and manufactured by Nihon Entegris G.K., can be used.

The foregoing filtration step can be performed before the pH of the quaternary alkylammonium hypochlorite solution is adjusted within an appropriate range for the intended use. In such a case, after the filtration step is performed once, mixing with the chlorine gas can be again performed to thereby adjust a quaternary alkylammonium hypochlorite solution having an objective pH. Mixing of water, an acid such as hydrogen chloride, and/or an alkali such as an aqueous quaternary tetramethylammonium hydroxide solution can also be performed to thereby adjust a quaternary alkylammonium hypochlorite solution having an objective pH. In a case where the pH of the quaternary alkylammonium hypochlorite solution produced is a pH suitable for a washing liquid, the solution can be filtered and the resultant can be adopted as it is in a washing liquid for use in production of a semiconductor element.

Such a filtration step can be performed to thereby decrease, in particular, metal components such as magnesium, iron, nickel, copper, silver, cadmium, and lead.

<Storage Step>

A solution containing halogen oxyacid (which will be hereinafter described with a quaternary alkylammonium hypochlorite solution as an example) obtained after a production method according to an embodiment of the present invention or through the production method further including the filtration step can be used as it is m predetermined applications such as a washing liquid, and is generally used after a storage step (including preservation and transport). The quaternary alkylammonium hypochlorite solution is inferior in storage stability in the form of a single substance, and there has been a need for addition of a stabilizer. However, a stabilizer may cause an organic residue to occur and any improvement has been required. A storage step described below can be further undergone to thereby allow a quaternary alkylammonium hypochlorite solution more enhanced in storage stability to be supplied.

A method for producing a quaternary alkylammonium hypochlorite solution, according to one embodiment of the present invention, preferably includes a storage step of storing the reaction liquid, after the above steps, and the pH at 25° C. of the quaternary alkylammonium hypochlorite solution in the storage step is preferably adjusted so as to be 12.0 or more and less than 14.0, more preferably 12.0 or more and 13.8 or less. In a case where the filtration step is included after the production method of the present invention, the storage step can also be included after the filtration step.

The concentration of the quaternary alkylammonium hypochlorite solution to be stored is not particularly limited, and the quaternary alkylammonium hypochlorite solution preferably contains 0.001 mass % or more and 20 mass % or less of hypochlorite ion and 0.001 mass % or more and 50 mass % or less of quaternary alkylammonium ion, at a predetermined pH, in consideration of industrial production. The "predetermined pH" refers to any pH of 12.0 or more and less than 14.0, selected as the pH in the storage step.

Other various additives can also be compounded in the quaternary alkylammonium hypochlorite solution, if desired, depending on the intended use. For example, a metal chelator, a complexation agent, a metal dissolution promoter, a metal corrosion inhibitor, a surfactant, an acid, an alkali, and/or the like can be added as such additives. Such additives can be added to thereby allow, for example, promotion or suppression of metal dissolution, an improvement in surface roughness, an enhancement in treatment rate, and reduction in attachment of particles, in a semiconductor wafer treatment, to be expected, and thus a washing liquid containing such any additive(s) can be suitably used in a semiconductor wafer treatment. A storage step of the quaternary alkylammonium hypochlorite solution, according to a preferable embodiment, involves storage of the quaternary alkylammonium hypochlorite solution within a limited pH range. The storage step will be hereinafter described in detail.

The "storage" here means any storage from the start of the storage at a pH at 25° C. of the quaternary alkylammonium hypochlorite solution, of 12.0 or more and 14.0 or less, in another aspect, 12.0 or more and 13.8 or less, to adjustment of the concentration and/or pH of the quaternary alkylammonium hypochlorite solution. In a case where the pH of the solution after pH adjustment is 12.0 or more and 14.0 or less, additional storage of the solution, if present, also corresponds to the storage step of the present embodiment. The quaternary alkylammonium hypochlorite solution, when the pH thereof is originally 12.0 or more and 14.0 or less, can be stored as it is, and, when the pH thereof is less than 12.0 or more than 14.0, the solution can be stored after the pH is adjusted within the range of 12.0 or more and 14.0 or less.

The pH of the solution can vary depending on the temperature. The pH is here a value at 25° C., as a guide. The liquid temperature in actual storage of the solution is not limited to 25° C. Accordingly, conditions in storage are not particularly limited, and storage is preferably performed in common storage conditions, namely, storage in a known container, a canister can, or a resin storage container at −25° C. or more and 50° C. or less, still more preferably performed in a dark place in a storage container capable of shielding light, a transport container such as a canister can, or a resin storage container, filled with an inert gas, at −20° C. or more and 40° C. or less. In a case where the storage temperature exceeds the range, hypochlorite ion may be pyrolyzed to form an oxygen molecule, to thereby cause expansion and breakage of such a container, during storage for a long period.

In a preferable embodiment, the quaternary alkylammonium hypochlorite solution stored is one where the pH at 25° C. is 12.0 or more and 14.0 or less. The pH range does not lead to a reduction in hypochlorite ion concentration and enables long-term storage. In a case where the pH is less than 12.0, a disproportionation reaction of hypochlorite ion progresses to cause the hypochlorite ion to be decomposed, to result in a decrease in oxidation power of the quaternary alkylammonium hypochlorite solution. In a case where the pH is more than 14.0, organic ion as cation is presumed to be decomposed. As a result, it is presumed that a disproportionation reaction of hypochlorite ion, which is inhibited due to bulkiness of the organic ion, again progresses to cause the hypochlorite ion to be decomposed. The quaternary alkylammonium hypochlorite solution stored is preferably one where the pH at 25° C. is 12.0 or more and 14.0 or less.

Although the reason for an enhancement in storage stability by the storage method is not clear, the present inventors presume the following. It is presumed that quaternary alkylammonium hypochlorite in the quaternary alkylammonium hypochlorite solution, while is partially dissociated into hypochlorite ion and organic ion, largely has an ionic bond of hypochlorite ion and organic ion. The steric bulkiness of organic ion is thought to suppress a disproportionation reaction of hypochlorite ion. It is thus considered that, as the steric bulkiness of organic ion is increased, the disproportionation reaction is suppressed to result in an enhancement in storage stability. The organic ion can sufficiently suppress the disproportionation reaction as long as it is bulky quaternary alkylammonium ion, for example, tetramethylammonium ion. The quaternary alkylammonium hypochlorite solution being stored is not almost changed in oxidation power even for a storage period of 30 days, preferably 60 days, still more preferably 90 days, as long as the solution undergoes the storage step according to the present embodiment. Accordingly, the quaternary alkylammonium hypochlorite solution can be used in various applications only by dilution after storage, depending on the usage conditions. As the storage period is a longer period, the effect of enhancing productivity can be expected.

<Halogen Oxyacid Solution Production Apparatus>

Next, an embodiment of a halogen oxyacid solution production apparatus will be described. The production method can be performed by use of a production apparatus of the present embodiment. One example of the production apparatus according to the present embodiment, here shown, is an example where a quaternary alkylammonium hydroxide solution is used as an organic alkali and a chlorine gas is used as halogen. Herein, the conditions described with respect to the method for producing halogen oxyacid, as described above, can be used, as these are, as conditions, for example, various compounds of an organic alkali and halogen supplied as raw materials, the concentration, the rate of supply and so on.

The production apparatus of the present embodiment is a production apparatus including a static mixer, an organic alkaline solution supply means and a halogen supply means to the static mixer, and a reaction liquid retrieve means for outwardly retrieving a reaction liquid from the static mixer, wherein an organic alkaline solution and halogen are continuously supplied respectively from the organic alkaline solution supply means and the halogen supply means to the static mixer, and mixed, to thereby generate a solution containing halogen oxyacid, as a reaction liquid, and the reaction liquid is continuously retrieved by the reaction liquid retrieve means.

FIG. 1 shows a schematic view of a production apparatus. In FIG. 1, the production apparatus includes a quaternary alkylammonium hydroxide solution supply pipe 1 as an organic alkali supply means, a chlorine gas supply pipe 2 as the halogen supply means, and a static mixer 3 and a reaction liquid retrieve pipe 5 located immediately thereafter. The static mixer 3 is used to mix a quaternary alkylammonium hydroxide solution and a chlorine gas. A production apparatus according to an embodiment of the present invention can include a heat exchanger 4 for removal of heat such as reaction heat. An aspect of the heat exchanger 4 can be exemplified where the exchanger is disposed downstream of the static mixer 3, and the exchanger can be disposed anywhere as long as reaction heat can be removed.

Both the quaternary alkylammonium hydroxide solution and the chlorine gas to be supplied are continuously supplied. A reaction liquid generated is continuously retrieved through the reaction liquid retrieve pipe 5.

The static mixer included in the production apparatus of the present invention, here used, can be one exemplified in the description of the production method. In particular, an ejector, a collision static mixer, or a Sulzer static mixer can be preferably exemplified.

The production apparatus of the present invention can further include one or more separate static mixers downstream of the static mixer (first static mixer) and upstream of the reaction liquid retrieve means, and can further include a halogen supply means for supplying halogen to each of the separate static mixers.

In a case where the production apparatus of the present invention includes two or more such static mixers, an aspect can be exemplified where a pipe is provided downstream of a first static mixer, the pipe is connected to a second static mixer, and the halogen supply means is provided so as to be connected to the second static mixer.

With reference to FIG. 1, an aspect can be exemplified where the reaction liquid retrieve pipe 5 is connected to a second static mixer (not shown) and a second halogen supply means (not shown) is separately connected to the second static mixer. In a case where the $n^{th}$ static mixer is disposed in the same manner, an aspect can be exemplified where a pipe is provided downstream of the $n-1^{th}$ static mixer, the pipe is connected to the $n^{th}$ static mixer, and the $n^{th}$ halogen supply means is provided so as to be connected to the $n^{th}$ static mixer (n is, for example, 2, 3, 4, 5, 6, 7, 8, 9 or 10).

For example, in a case where the production apparatus of the present invention further includes a third static mixer, an aspect can be exemplified where a pipe is provided downstream of the second static mixer, the pipe is connected to the third static mixer, and a third halogen supply means is provided so as to be connected to the third static mixer.

In a case where the production apparatus of the present invention includes a plurality of such static mixers, the reaction liquid is not required to necessarily flow through all the static mixers, by designing a flow channel and/or providing a valve.

In a case where the production apparatus of the present invention includes a plurality of such static mixers, fresh halogen can be contacted with the reaction liquid passed through the initial static mixer, at multiple stages. Thus, the unreacted organic alkali contained in the reaction liquid can be reacted with such fresh halogen, to thereby allow a reaction for obtaining halogen oxyacid to occur at multiple stages. In an aspect where a production apparatus according to an embodiment of the present invention includes a plurality of such static mixers, the number of such static mixers can be, for example, 2, 3, 4, or 5 or more. The upper limit is not particularly limited, and can be, for example 10 or less.

The production apparatus of the present invention can have a configuration where the reaction liquid is circulated in the production apparatus by adjustment of the flow channel of the reaction liquid even in a case where one static mixer is included or two or more static mixers are included. In order that the reaction liquid is circulated in the production apparatus, adjustment can be made so that the retrieve pipe of the reaction liquid is branched and/or any pipe between a plurality of such static mixers is branched to thereby connect a pipe as a branch destination to the static mixer where passing through of the reaction liquid is conducted once. Such a configuration can allow the unreacted organic alkali contained in the reaction liquid and fresh halogen to be reacted in one production apparatus, and can allow the reaction to be performed at multiple stages.

The reaction liquid can also be retrieved with being not circulated in the production apparatus in a case where the production apparatus of the present invention does not have the above configuration or has the above configuration but has an appropriate valve provided therein.

The conditions described with respect to the production method can be used, as these are, in those of the inside surface of the static mixer shown in FIG. 1.

Each of the flow rates of the quaternary alkylammonium hydroxide solution supplied and the reaction liquid in the pipe is preferably 0.01 n/s or more and 10 m/s or less, more preferably 0.2 m/s or more and 3 m/s or less.

An aspect is suitable where the volume of the static mixer is a volume so that the liquid stay time of the quaternary alkylammonium hydroxide solution supplied is 0.1 minutes or more and 5 minutes or less. The liquid stay time is more preferably 0.1 minutes or more and 1 minute or less.

The reaction of the quaternary alkylammonium hydroxide solution and the chlorine gas is an exothermal reaction. In a production apparatus according to an embodiment of the present invention, the heat exchanger 4 can be disposed downstream of the static mixer, to thereby perform removal of heat. The heat exchanger is not limited to be disposed downstream of the static mixer. The heat exchanger can be disposed, to thereby adjust the temperature of the reaction liquid to, for example, 23° C. or more and 27° C. or less, preferably 24° C. or more and 26° C. or less.

The reaction liquid retrieved through the retrieve pipe 5 of the reaction liquid can be sent to a product preparation section (not shown). The product preparation section allows for adjustment of the concentration and the pH of the reaction liquid sent from the static mixer. The product preparation section allows for adjustment of the concentration and the pH of the reaction liquid, if necessary, by supplying any one or more of the organic alkaline solution, for example, the quaternary alkylammonium hydroxide solution, hydrochloric acid, and water. Examples of the configuration of the product preparation section can include a tank having a sufficient volume so that not only the reaction liquid, but also any one or more of the quaternary alkylammonium hydroxide solution, hydrochloric acid, and water are supplied.

In a production apparatus according to an embodiment of the present invention, a filtration apparatus can be provided upstream or downstream of the product preparation section. Examples of the configuration of the filtration apparatus can include a configuration including a reaction liquid transfer tube, a pump, a filtration filter, and a reaction liquid return tube. Such each member in the filtration apparatus is contacted with a reaction liquid containing quaternary alkylammonium hypochlorite, and thus is preferably formed by the organic polymer material. The filtration filter here used can be one exemplified with respect to the filtration step.

The production apparatus of the present embodiment can further include an organic alkaline solution preparation section for preparing an organic alkaline solution to be supplied to the static mixer and/or the product preparation section. An organic alkali as a raw material, and water are supplied to the organic alkaline solution preparation section. The organic alkaline solution preparation section allows for adjustment of the concentration and the pH of the organic alkaline solution. Examples of the configuration of the organic alkaline solution preparation section can include a tank including a pipe for supplying the organic alkali, a pipe for supplying water, and a retrieve pipe for retrieving the prepared organic alkaline solution. The organic alkaline solution retrieved from the retrieve pipe is supplied through a pipe through which the organic alkaline solution flows, toward the static mixer or the product preparation section. The organic alkali preparation section can include a circulating temperature control means in order that the temperature of the solution in the preparation section is controlled. Examples of the circulating temperature control means can include one having a configuration including a pipe through which a portion of the organic alkaline solution retrieved from the retrieve pipe flows, a heat exchanger for heat exchange of the organic alkaline solution supplied from the pipe, a pipe for returning the organic alkaline solution whose temperature is controlled through the heat exchanger, to the organic alkaline solution preparation section, and a pump for circulating the organic alkaline solution.

The organic alkaline solution preparation section can include a means for supplying nitrogen into the preparation section, in order that the concentration of a gas component in a gas phase portion in the preparation section is adjusted. Examples of such a nitrogen supply means include one having a configuration including a pump for supplying nitrogen from the outside to the inside of the preparation section, and a pipe through which nitrogen flows.

EXAMPLES

Next, the present invention will be described in detail with reference to Examples and Comparative Examples, but the present invention is not limited to such Examples.

<Method for Measuring pH>

Thirty mL of a quaternary alkylammonium hydroxide solution and 30 mL of a quaternary alkylammonium hypochlorite solution were subjected to pH measurement with a tabletop pH meter (LAQUA F-73, manufactured by HORIBA. Ltd.). The measurement of the pH was carried out after stabilization at 25° C.

<Method for Calculating Effective Chlorine Concentration and Hypochlorite Ion Concentration>

To a 100 mL Erlenmeyer flask were added 0.5 mL of a treatment liquid (quaternary alkylammonium hypochlorite solution), 2 g of potassium iodide (special grade reagent; manufactured by FUJIFILM Wako Pure Chemical Corporation), 8 mL of 10 mass % acetic acid and 10 mL of ultrapure water, and the resultant was stirred until the solids were dissolved, to obtain a brown solution.

The brown solution prepared was subjected to redox titration using a 0.02 M sodium thiosulfate solution (for volumetric analysis; manufactured by FUJIFILM Wako Pure Chemical Corporation) until the color of the solution turned from brown to very pale yellow. Subsequently, a starch solution was added to the resultant, to obtain a pale purple solution.

The 0.02 M sodium thiosulfate solution was further added continuously to the resulting solution, and the effective chlorine concentration was calculated, taking the point at which the solution turned colorless and transparent, as the end point. Further, a hypochlorite ion concentration was calculated from the obtained effective chlorine concentration. For example, when the effective chlorine concentration was 1 mass %, the hypochlorite ion concentration was 0.73 mass %.

<Yield of Chlorine>

The yield of chlorine was determined from the ratio (%) of the number of moles of hypochlorite ion generated, to the number of moles of a chlorine molecule supplied. In a case where the whole amount of chlorine added was reacted (no occurrence of decomposition), the yield of chlorine was defined as 100%. In a case where hypochlorite ion was decomposed in the reaction, the yield of chlorine was decreased.

<Method for Evaluating Storage Stability>

After the quaternary alkylammonium hypochlorite solution was placed into a glove bag and the carbon dioxide concentration in the glove bag reached 1 ppm or less, the solution was transferred to a PFA (perfluoroalkoxyfluororesin, tetrafluoroethylene-perfluoroalkyl vinyl ether copolymer) container, and the container was sealed. Subsequently, the resultant was stored under a light shielding environment at 23° C. for 10 days, and thereafter the hypochlorite ion concentration of the quaternary alkylammonium hypochlorite solution in the PFA container was measured. A ratio of hypochlorite ion concentration (Concentration after 10 days/Initial concentration), of 60% or more and 100% or less, was rated as "Favorable", and a ratio of less than 60% was rated as "Poor".

Example 1

An 8.6 mass % tetramethylammonium hydroxide solution having a pH of 14.1 was supplied at 1 kg/min, through a pipe having a diameter of 6 mm, a chlorine gas was supplied at 0.29 mol/min in the middle of a flow channel, and thereafter these were mixed by use of a static mixer. Thereafter, the resulting mixture was cooled by a PFA heat exchanger having a pipe diameter of 6 mm and a length of 7.9 m, manufactured by AS ONE Corporation, and kept at 25° C., to obtain a tetramethylammonium hypochlorite solution. The reaction volume including the heat exchanger was 0.7 L. Here, the yield of chlorine was 98%, the pH was 13.6, the effective chlorine concentration was 1.9 mass %, and the amount of production was 1 L/min per 0.7 L. The storage stability was favorable.

Example 2

The same manner as in Example 1 was performed except that the chlorine gas was supplied at two stages, in order to observe the influence of supply of chlorine at multiple stages.

Here, the yield of chlorine was 99%, the pH was 13.6, the effective chlorine concentration was 1.9 mass %, and the amount of production was 1 L/min per 0.7 L. The storage stability was favorable.

Example 3

Almost the same manner as in Example 1 was performed in order to observe the influence of the pH of the raw material.

A 2.9 mass % tetramethylammonium hydroxide solution having a pH of 13.6 was supplied at 1 kg/min, through a pipe having a diameter of 6 mm, a chlorine gas was supplied at 0.070 mol/min in the middle of a flow channel, and thereafter these were mixed by use of a static mixer. Thereafter, the resulting mixture was cooled by a PFA heat exchanger having a pipe diameter of 6 mm and a length of 7.9 m, manufactured by AS ONE Corporation, and kept at 25° C. to obtain a tetramethylammonium hypochlorite solution. Here, the yield of chlorine was 92%, the pH was 13.5, the effective chlorine concentration was 0.41 mass %, and the amount of production was 1 L/min per 0.7 L. The storage stability was favorable.

Example 4

Almost the same manner was performed except that 0.15 mol/min of the chlorine gas in Example 3 was supplied, in order to observe the influence of the pH of the raw material.

Here, the yield of chlorine was 99%, the pH was 12.7, the effective chlorine concentration was 0.83 mass %, and the amount of production was 1 L/min per 0.7 L. The storage stability was favorable.

Comparative Example

Experimental Example in the case of use of a batch reaction was shown as Comparative Example.

A cylindrical reactor having a diameter of 190 mm was charged with 10,000 ml of an 8.6 mass % tetramethylammonium hydroxide solution having a pH of 14.0, and chlorine was supplied at 17.7 mmol/min with liquid circulation in the reactor at 500 ml/min by a circulation pump mounted to the reactor. A quaternary tetramethylammonium hypochlorite solution generated was retrieved at a liquid stay time in the reactor, of 256 min. The reaction temperature was 25° C. The effective chlorine concentration was 2.9 mass %, the pH was 12.9, and the yield of chlorine was 91%, in the quaternary tetramethylammonium hypochlorite solution generated. The storage stability was poor.

The reaction conditions and results were summarized in Tables 1 and 2.

TABLE 1

|  | TMAH concentration [mass %] | TMAH pH | Flow rate of TMAH [m/s] | Amount of chlorine supplied [mmol/min] | Number of divisions of chlorine supply |
|---|---|---|---|---|---|
| Example 1 | 8.6 | 14.1 | 0.4 | 0.29 | 1 |
| Example 2 | 8.6 | 14.1 | 0.4 | 0.29 | 2 |
| Example 3 | 2.9 | 13.6 | 0.4 | 0.07 | 1 |
| Example 4 | 2.9 | 13.6 | 0.4 | 0.15 | 1 |
| Comparative Example | 8.6 | 14.1 | — | 0.018 | — |

TABLE 2

|  | Effective chlorine concentration [mass %] | Yield of chlorine [%] | Storage stability | Amount of liquid obtained, per time [L/min] |
|---|---|---|---|---|
| Example 1 | 1.9 | 98 | Favorable | 1.1 |
| Example 2 | 1.9 | 99 | Favorable | 1.1 |
| Example 3 | 0.41 | 92 | Favorable | 1.1 |
| Example 4 | 0.83 | 99 | Favorable | 1.1 |
| Comparative Example | 2.9 | 91 | Poor | 0.039 |

DESCRIPTION OF SYMBOLS

1 quaternary alkylammonium hydroxide solution supply pipe
2 halogen supply pipe
3 static mixer
4 heat exchanger
5 quaternary alkylammonium hypohalite solution retrieve pipe

The invention claimed is:

1. A method for producing a halogen oxyacid solution, comprising continuously supplying an organic alkaline solution and halogen to a static mixer and mixing them, to thereby continuously obtain a halogen oxyacid generated.

2. The method for producing a halogen oxyacid solution according to claim 1, wherein a ratio of raw materials supplied is controlled so that a pH at 25° C. of a mixed liquid of the organic alkaline solution and halogen passed through the static mixer is more than 10.5 and less than 14.1.

3. The method for producing a halogen oxyacid solution according to claim 2, wherein the pH at 25° C. of the mixed liquid is 12.0 or more and 13.8 or less.

4. The method for producing a halogen oxyacid solution according to claim 1, wherein the halogen is supplied at multiple stages.

5. The method for producing a halogen oxyacid solution according to claim 1, wherein the mixing is performed at multiple stages.

6. The method for producing a halogen oxyacid solution according to claim 1, wherein the static mixer is an ejector, a collision type static mixer, or a Sulzer static mixer.

7. The method for producing a halogen oxyacid solution according to claim 1, wherein the halogen oxyacid solution is retrieved without being circulated in a production process.

8. The method for producing a halogen oxyacid solution according to claim 1, wherein a pH at 25° C. of the organic alkaline solution is 10.5 or more and 14.5 or less.

9. The method for producing a halogen oxyacid solution according to claim 1, wherein the organic alkali is onium hydroxide and the halogen oxyacid is halogen oxyacid onium.

10. The method for producing a halogen oxyacid solution according to claim 9, wherein the onium hydroxide is quaternary alkylammonium hydroxide and the halogen oxyacid onium is quaternary ammonium hypohalite.

11. The method for producing a halogen oxyacid solution according to claim 10, wherein the quaternary alkylammonium hydroxide is tetramethylammonium hydroxide.

12. The method for producing a halogen oxyacid solution according to claim 1, wherein the halogen is chlorine, bromine, hypochlorous acid, hypobromous acid, chlorous acid, bromous acid, chloric acid, bromic acid, iodine, hypoiodous acid, iodous acid, or iodic acid.

13. The method for producing a halogen oxyacid solution according to claim 1, wherein the halogen is chlorine.

14. A halogen oxyacid solution production apparatus comprising a static mixer, an organic alkaline solution supply means and a halogen supply means to the static mixer, and a reaction liquid retrieve means for outwardly retrieving a reaction liquid from the static mixer, wherein
    an organic alkaline solution and halogen are continuously supplied respectively from the organic alkaline solution supply means and the halogen supply means to the static mixer, and mixed, to thereby generate a halogen oxyacid solution as a reaction liquid, and the reaction liquid is continuously retrieved by the reaction liquid retrieve means.

15. The halogen oxyacid solution production apparatus according to claim 14, further comprising one or more separate static mixers downstream of the static mixer and upstream of the reaction liquid retrieve means, and further comprising a halogen supply means for supplying halogen to each of the separate static mixers.

16. The halogen oxyacid solution production apparatus according to claim 14, further comprising a heat exchanger that performs heat exchange of the reaction liquid.

\* \* \* \* \*